United States Patent [19]

Ikeda et al.

[11] Patent Number: 5,422,102
[45] Date of Patent: * Jun. 6, 1995

[54] ANTIINFLAMMATORY AND ANALGESIC GEL PREPARATION

[75] Inventors: Yasuo Ikeda, Narashino; Shuichi Kasai; Satoru Enomoto, both of Narita; Katsumi Imamori; Akira Iwasa, both of Yotsukaido, all of Japan

[73] Assignee: SS Pharmaceutical Co., Ltd., Tokyo, Japan

[ * ] Notice: The portion of the term of this patent subsequent to Sep. 27, 2011 has been disclaimed.

[21] Appl. No.: 109,257

[22] Filed: Aug. 20, 1993

[30] Foreign Application Priority Data

Dec. 4, 1992 [JP] Japan ................... 4-325632

[51] Int. Cl.$^6$ ........................ A61K 31/74; A61L 15/44
[52] U.S. Cl. .................. 424/78.05; 424/445; 514/887; 514/944; 514/947
[58] Field of Search ............................ 424/78.05, 445; 514/887, 944, 947

[56] References Cited

U.S. PATENT DOCUMENTS 4,789,667 12/1988 Makino et al. ...................... 514/947

FOREIGN PATENT DOCUMENTS 60-48921 3/1985 Japan .
63-8329 1/1988 Japan .
63-287721 11/1988 Japan .
3-291222 12/1991 Japan .

Primary Examiner—Thurman K. Page
Assistant Examiner—Carlos Azpuru
Attorney, Agent, or Firm—Oblon, Spivak, McClelland, Maier & Neustadt

[57] ABSTRACT

An antiinflammatory and analgesic gel preparation comprising diclofenac or its salts, an ester of dibasic acid, a lower alcohol, and a nonionic polymer or a mixture of nonionic polymers selected from the group consisting of (a) 1.5-4% by weight of hydroxypropyl cellulose having a molecular weight of 500,000 or greater, (b) 2-4% by weight of hydroxyethyl cellulose having a molecular weight of 1,250,000 or greater, and (c) 1.5-4% by weight of a mixture of hydroxypropyl cellulose having a molecular weight of 500,000 or greater and hydroxyethyl cellulose having a molecular weight of 1,250,000 or greater, and having a viscosity of 5,000-35,000 cps and an yield value of 5 dyn/cm$^2$ or greater. The gel preparation is excellent in the percutaneous absorption of diclofenac or its salts and provides good properties upon use and superior medical effects of diclofenac or its salts.

5 Claims, No Drawings

ANTIINFLAMMATORY AND ANALGESIC GEL PREPARATION

BACKGROUND OF THE INVENTION

1. Field of the Invention

The present invention relates to an antiinflammatory and analgesic gel preparation exhibiting excellent percutaneous absorption and good properties upon use.

2. Description of the Background Art

Diclofenac or its salts possess excellent antiinflammatory and analgesic action, and are widely used in clinics in an oral or rectal dosage form. When administered orally or rectally, they are known to cause various side effects, including gastrointestinal tract disturbance. Because of this reason, a preparation for external application has been proposed, by which the drug is percutaneously absorbed without going through gastrointestinal tract and exerts its action locally or systemically. However, since diclofenac and its salts are scarcely absorbed percutaneously, such a preparation had not been commercially sold.

Gel preparations, on the other hand, possess an advantage over other preparations for external application in terms of the good feeling upon use. When a gel preparation contains diclofenac or its salts as an active ingredient, there are problems that a high concentration of diclofenac or its salts may destroy the gel structure, and fluidize the gel or crystallize diclofenac or its salts over time.

The present inventors previously filed a patent application (WO92/07561) based on the finding that a gel preparation in which diclofenac or its salts are contained at a high concentration and in a stable manner can be obtained, if base components comprising a dibasic acid ester and a lower alcohol are gelatinized by using a nonionic polymer as a gelling agent.

The gel preparation, however, was not still satisfactory in its percutaneous absorption of diclofenac or its salts and properties upon use.

Development of an antiinflammatory and analgesic gel preparation which can exhibit excellent percutaneous absorption of diclofenac or its salts and good properties upon use has therefore been desired.

In view of this situation the present inventors have undertaken extensive studies and found that an antiinflammatory and analgesic gel preparation which can exhibit excellent percutaneous absorption of diclofenac or its salts and good properties upon use can be obtained by formulating a specific type of nonionic polymer into a composition comprising diclofenac or its salts, an ester of dibasic acid, and a lower alcohol, and by adjusting the viscosity and the yield value of the composition in specific ranges. The finding has led to the completion of the present invention.

SUMMARY OF THE INVENTION

Accordingly, an object of the present invention is to provide an antiinflammatory and analgesic gel preparation comprising diclofenac or its salts, an ester of dibasic acid, a lower alcohol, and a nonionic polymer selected from the group consisting of, (a) 1.5–4% by weight of hydroxypropyl cellulose having a molecular weight of 500,000 for greater, (b) 2–4% by weight of hydroxyethyl cellulose having a molecular weight of 1,250,000 or greater, and (c) 1.5–4% by weight of a mixture of hydroxypropyl cellulose having a molecular weight of 500,000 or greater and hydroxyethyl cellulose having a molecular weight of 1,250,000 or greater, and having a viscosity of 5,000–35,000 cps and an yield value of 5 $dyn/cm^2$ or greater.

DETAILED DESCRIPTION OF THE INVENTION AND PREFERRED EMBODIMENTS

There are no specific restrictions as to the salts of diclofenac, so long as they are pharmaceutically acceptable compounds. Given as examples of such salts are salts of alkali metal, alkaline earth metal, ammonia, and primary, secondary, or tertiary alkylamine or alkanolamine; e.g., sodium, potassium, calcium, ammonium, dimethylamine, diethylamine, trimethylamine, triethylamine, monoethanolamine, diethanolamine, diisopropanolamine, triethanolamine, triisopropanolamine, and the like. Especially preferable salts are sodium salt and ammonium salt. There are no limitations to the amount of diclofenac or its salts in the preparation; it may be the amount by which the medicinal effect is exhibited. Generally, an amount of 0.1–20% by weight, especially 0.5–10% by weight, is preferable.

As esters of dibasic acid, those soluble in a mixed solvent of a lower alcohol and water and capable of promoting the skin permeability of diclofenac or its salts are preferable. Specific examples are diisopropyl adipate, diisopropyl sebacate, diethyl sebacate, and the like. They may be either used individually or two or more of them may be used together. The amount of esters of dibasic acid to be incorporated should be sufficient to achieve the desired absorption of diclofenac or its salts. Generally, an amount of 0.5–20% by weight, especially 1.5–10% by weight, is preferable.

Any lower alcohols which are pharmaceutically acceptable may be used without specific limitations. Examples which may be given include ethyl alcohol, isopropyl alcohol, and a mixture of them. The amount of lower alcohol to be incorporated into the preparation varies depending on the types of nonionic polymer incorporated, pH of the preparation, types of diclofenac or its salts and other liquid components. Generally, an amount of 10–80% by weight, especially 25–70% by weight, is preferable.

Incorporated into the composition of the present invention is a nonionic polymer selected from the group consisting of, (a) 1.5–4% by weight of hydroxypropyl cellulose having a molecular weight of 500,000 or greater, (b) 2–4% by weight of hydroxyethyl cellulose having a molecular weight of 1,250,000 or greater, (c) 1.5–4% by weight of a mixture of hydroxypropyl cellulose having a molecular weight of 500,000 or greater and hydroxyethyl cellulose having a molecular weight of 1,250,000 or greater.

If the molecular weights of the above nonionic polymers are less than defined, no gel preparation having the desired viscosity and yield value can be obtained. Furthermore, if the amounts of these nonionic polymers are smaller than the amounts defined above, no gel preparation having a satisfactory viscosity and yield value can be obtained. If the amounts exceed the amounts defined above, on the other hand, the gel preparation has a too high viscosity and provides unacceptable properties upon use.

Given of commercially available nonionic polymers having a preferable molecular weight range are, as hydroxypropyl cellulose, MF (trade mark, a product of Hercules), HF (trade mark, a product of Hercules), and like; and as hydroxyethyl cellulose, CF-W (trade mark, a product of Fuji Chemical), CF-X (trade mark, a product of Fuji Chemical), and the like.

If the pH of the gel preparation of the present invention is in considerably basic or acidic side, its repeated application to the same site may cause unstable percutaneous absorption of diclofenac or its salts or may give undesirable adverse side effects such as irritation to the skin. Furthermore, since the solubility of diclofenac or its salts in a solvent is affected by its pH, the change of pH may cause diclofenac or its salts to crystallize over time. Because of these reasons, it is desirable to add a pH modifier to the preparation of the present invention to adjust its pH in the range of 5-8.5, preferably 5.5-8. There are no specific limitations as to the kind of the pH modifiers inasmuch as they are capable of adjusting the pH within the above range. Given as examples of such pH modifiers are inorganic pH modifiers, e.g., hydrochloric acid, sodium hydroxide, and potassium hydroxide; and organic acid, e.g., acetic acid, lactic acid, citric acid, malic acid, tartaric acid, maleic acid, fumaric acid, adipic acid, salicylic acid, and the like, as well as their salts. They may be either used individually or tow or more of them may be used together. Furthermore, an acidic pH modifier and basic pH modifier may be used together to provide a buffering effect.

There are no specific limitations to the method of preparing the preparation of the present invention. Generally, a preferable method comprises mixing liquid components, adding diclofenac or its salts to the mixture to dissolve it thereinto, adjusting pH by the addition of the pH modifier, followed by a slow addition of the nonionic polymer while stirring to obtain a gel preparation. Other methods may be employed conforming to the characteristics of the gel formulation, equipment to be used, and the like. To the preparation of the present invention, may optionally be added moisturizing agents, solubilizers, stabilizers, perfumes, coloring agents, and the like; and if required for controlling the skin permeability of diclofenac or its salts or improving the feeling upon use, may further be added other components which are commonly used in external dosage forms such as surface active agents, urea, methyl salicylate, crotamiton, menthol, and the like. Of the above optional components, addition of 0.02-1% by weight, preferably 0.05-0.5% by weight, of sodium sulfite, sodium sulfite anhydride, hydrogen sodium sulfite, sodium pyrosulfite, sodium thiosulfate, Rongalit, or the like, as a stabilizer, provides a desirable composition.

The gel preparation composition of the present invention prepared by the above method has a viscosity of 5,000-35,000 cps at 25° C. and an yield value of 5 dyn/cm$^2$ or greater. The gel preparation exhibits an especially excellent percutaneous absorption of diclofenac or its salts and good properties upon use when the viscosity and the yield value are within the above range. If the viscosity is less than 5,000 cps, the gel is liquefied when applied, failing to properly cover the applied site of the skin; if it is greater than 35,000 cps, the feeling upon use is deteriorated because it is sticky to the touch. A gel composition having an yield value of smaller than 5 dyn/cm$^2$ may not be able to stay on applied site when applied to the skin.

Other features of the invention will become apparent in the course of the following description of the exemplary embodiments which are given for illustration of the invention and are not intended to be limiting thereof.

EXAMPLES

Example 1

Gel preparations of the compositions shown in Tables 1-3 were prepared to measure their viscosity and yield value.

Isopropyl alcohol, diisopropyl adipate, and a portion of purified water were mixed, and diclofenac sodium was dissolved to the solution, and then were added hydroxyethyl cellulose and hydroxypropyl cellulose. After stirring to become in a homogeneous state, the mixture was adjusted to about pH 7 with the addition of lactic acid. The remaining water was added to make total volume 100 g to obtain a gel composition.

<Measurement method>

Viscosity: measured by using an E-type (cone-and-plate type) viscometer at 25.0° C., a gap angle of 3°28′, and a rotation of 5 rpm.

Yield value: Casson yield values were determined by applying the viscosity measured by using an E-type (cone-and-plate type) viscometer according to the above method to the following formula.

$$\sqrt{S} = \sqrt{Sc} + \sqrt{\mu_c D}$$

wherein S is shear stress, D is shear rate, Sc is the Casson yield value, and $\mu_c$ is Casson viscosity.

The results are shown in Table 1.

TABLE 1

| Component | Invention Product | | | | | Comparative Product | | | |
|---|---|---|---|---|---|---|---|---|---|
| | 1 | 2 | 3 | 4 | 5 | 1 | 2 | 3 | 4 |
| Diclofenac sodium | 1.00 | 1.00 | 1.00 | 1.00 | 1.00 | 1.00 | 1.00 | 1.00 | 1.00 |
| Diisopropyl adipate | 5.00 | 5.00 | 5.00 | 5.00 | 5.00 | 5.00 | 5.00 | 5.00 | 5.00 |
| Lactic acid | 0.04 | 0.04 | 0.04 | 0.04 | 0.04 | 0.04 | 0.04 | 0.04 | 0.04 |
| isopropyl alcohol | 40.00 | 40.00 | 40.00 | 40.00 | 40.00 | 40.00 | 40.00 | 40.00 | 40.00 |
| Hydroxypropyl cellulose (H)[1] | — | — | — | — | — | 4.00 | 5.00 | — | — |
| Hydroxypropyl cellulose (MF)[2] | 2.00 | 3.00 | 4.00 | — | — | — | — | 5.00 | — |
| Hydroxypropyl cellulose (HF)[3] | — | — | — | 1.50 | 2.00 | — | — | — | 1.00 |
| Purified water | 51.96 | 50.96 | 49.96 | 52.46 | 51.96 | 49.96 | 48.96 | 48.96 | 52.96 |
| Viscosity (cps, 5 rpm, 25° C.) | 5300 | 14200 | 26700 | 5200 | 9933 | 4300 | 8900 | 42233 | 1147 |

TABLE 1-continued

| Component | Invention Product | | | | | Comparative Product | | | |
|---|---|---|---|---|---|---|---|---|---|
| | 1 | 2 | 3 | 4 | 5 | 1 | 2 | 3 | 4 |
| Yield Value (dyn/cm$^2$) | 5.15 | 17.06 | 54.61 | 6.55 | 12.46 | 0.74 | 2.86 | 152.22 | 1.64 |

[1)] Average molecular weight, 300,000 (a product of Nippon Soda Co.)
[2)] Average molecular weight, 600,000
[3)] Average molecular weight, 1,000,000

TABLE 2

| Component | Invention Product | | | Comparative Product | | |
|---|---|---|---|---|---|---|
| | 6 | 7 | 8 | 5 | 6 | 7 |
| Diclofenac sodium | 1.00 | 1.00 | 1.00 | 1.00 | 1.00 | 1.00 |
| Diisopropyl adipate | 5.00 | 5.00 | 5.00 | 5.00 | 5.00 | 5.00 |
| Lactic acid | 0.04 | 0.04 | 0.04 | 0.04 | 0.04 | 0.04 |
| Isopropyl alcohol | 40.00 | 40.00 | 40.00 | 40.00 | 40.00 | 40.00 |
| Hydroxyethyl cellulose (CF-X)$^{1)}$ | 2.00 | — | — | 1.5 | 5.00 | — |
| Hydroxyethyl cellulose (CF-W)$^{2)}$ | — | 3.00 | 4.00 | — | — | — |
| Hydroxyethyl cellulose (SP-750)$^{3)}$ | — | — | — | — | — | 4.00 |
| Purified water | 51.96 | 50.96 | 49.96 | 52.46 | 48.96 | 49.96 |
| Viscosity (cps, 5 rpm, 25° C.) | 9400 | 5800 | 34900 | 3236 | 43333 | 3700 |
| Yield Value (dyn/cm$^2$) | 24.68 | 8.35 | 110.46 | 15.37 | 300.05 | 6.60 |

[1)] Average molecular weight, 2,300,000
[2)] Average molecular weight, 1,270,000
[3)] Average molecular weight, 1,210,000 (a product of Daicell Chemical Industry)

TABLE 3

| Component | Invention Product | | | Comparative Product | |
|---|---|---|---|---|---|
| | 9 | 10 | 11 | 8 | 9 |
| Diclofenac sodium | 1.00 | 1.00 | 1.00 | 1.00 | 1.00 |
| Diisopropyl adipate | 5.00 | 5.00 | 5.00 | 5.00 | 5.00 |
| Lactic acid | 0.04 | 0.04 | 0.04 | 0.04 | 0.04 |
| Isopropyl alcohol | 40.00 | 40.00 | 40.00 | 40.00 | 40.00 |
| Hydroxyethyl cellulose (CF-X)$^{1)}$ | 0.50 | 1.00 | 1.50 | 0.50 | 2.50 |
| Hydroxypropyl cellulose (HF)$^{2)}$ | 1.50 | 1.00 | 0.50 | 0.50 | 2.50 |
| Purified water | 51.96 | 51.96 | 51.96 | 52.96 | 48.96 |
| Viscosity (cps, 5 rpm, 25° C.) | 8267 | 7267 | 5800 | 1967 | 68433 |
| Yield Value (dyn/cm$^2$) | 15.29 | 12.04 | 11.02 | 1.15 | 337.07 |

[1)] Average molecular weight, 2,300,000
[2)] Average molecular weight, 1,000,000

Test Example 1

Percutaneous absorption of diclofenac of Invention Product 10 and Comparative Products 8 and 9 was examined.

Samples, 1.0 g each, were applied to the shaved back of Hartley guinea pigs (male, body weight: about 500 g) to measure diclofenac concentrations in plasma after 2, 4 and 6 hours of application by the HPLC method. The results are shown in Table 4.

TABLE 4

| | Diclofenac Concentrations in plasma (μg/ml) | | |
|---|---|---|---|
| Time (hour) | Invention Product 10 | Comparative Product 8 | Comparative Product 9 |
| 0 | 0.00 | 0.00 | 0.00 |
| 2 | 0.12 | 0.04 | 0.01 |
| 4 | 0.13 | 0.06 | 0.02 |
| 6 | 0.11 | 0.06 | 0.02 |

As can be seen from the results shown in Table 4, the gel preparation of the present invention exhibited higher concentrations of diclofenac in plasma, showing that it has excellent percutaneous absorption of diclofenac.

The gel preparation of the present invention has also good feeling upon use, while the gel Comparative Product 8 was liquefied upon use and Comparative Product 9 was sticky, demonstrating that the both were inferior in the feeling upon use.

Test Example 2

Invention Product 12 was prepared by adding 0.05 g of sodium pyrosulfite to Invention Product 10 obtained in Example 1. The products were stored at 50° C. for 1 month to examine the stability of diclofenac sodium over time to prove that all gel preparations were stable. The product to which sodium pyrosulfite was added was especially stable.

Example 2

The gel preparations were prepared by using diisopropyl sebacate or diethyl sebacate instead of diisopropyl adipate and ethyl alcohol instead of isopropyl alcohol of Invention Product 10 in Example 1.

The gel preparation obtained exhibited excellent percutaneous absorption of diclofenac and good properties upon use.

As illustrated above, the antiinflammatory and analgesic gel preparation of the present invention is excellent in its percutaneous absorption of diclofenac or its salts and good properties upon use, thus providing sufficient medical effects of diclofenac or its salts.

Obviously, numerous modifications and variations of the present invention are possible in light of the above teachings. It is therefore to be understood that within the scope of the appended claims, the invention may be practiced otherwise than as specifically described herein.

What is claimed is:

1. An antiinflammatory and analgesic gel preparation comprising from 0.1 to 20% by weight of diclofenac or its pharmaceutically acceptable salts, from 0.5 to 20% by weight of an ester of a dibasic acid, from 10 to 80% by weight of a lower alcohol, and a nonionic polymer selected from the group consisting of,
   (a) 1.5–4% by weight of hydroxypropyl cellulose having a molecular weight of 500,000 or greater,
   (b) 2–4% by weight of hydroxyethyl cellulose having a molecular weight of 1,250,000 or greater, and
   (c) 1.5–4% by weight of a mixture of hydroxypropyl cellulose having a molecular weight of 500,000 or greater and hydroxyethyl cellulose having a molecular weight of 1,250,000 or greater, and having a viscosity of 5,000–35,000 cps and an yield value of 5 dyn/cm$^2$ or greater.

2. The antiinflammatory and analgesic gel preparation according to claim 1, wherein the salt of diclofenac is diclofenac sodium or diclofenac ammonium.

3. The antiinflammatory and analgesic gel preparation according to claim 1, wherein said ester of dibasic acid is one or more members selected from the group consisting of diisopropyl adipate, diisopropyl sebacate, and diethyl sebacate.

4. The antiinflammatory and analgesic gel preparation according to claim 1, wherein said lower alcohol is ethyl alcohol, isopropyl alcohol, or a mixture of them.

5. The antiinflammatory and analgesic gel preparation according to claim 1, comprising, as the nonionic polymer, 1.5–4% by weight of a mixture of hydroxypropyl cellulose having a molecular weight of 500,000 or greater and hydroxyethyl cellulose having a molecular weight of 1,250,000 or greater.

* * * * *